(12) United States Patent
Chang et al.

(10) Patent No.: US 7,910,339 B2
(45) Date of Patent: Mar. 22, 2011

(54) PROCESS FOR PRODUCING POLYSACCHARIDE GUM

(75) Inventors: Peter R. Chang, Saskatoon (CA); Debbie P. Anderson, Saskatoon (CA); Tara C. McIntosh, Saskatoon (CA); Neil D. Westcott, Saskatoon (CA)

(73) Assignee: Her Majesty the Queen in right of Canada as represented by the Minister of Agriculture and Agri-Food Canada, Saskatchewan (CA)

( * ) Notice: Subject to any disclaimer, the term of this patent is extended or adjusted under 35 U.S.C. 154(b) by 391 days.

(21) Appl. No.: 11/996,072

(22) PCT Filed: Jul. 12, 2006

(86) PCT No.: PCT/CA2006/001136
§ 371 (c)(1),
(2), (4) Date: Jun. 10, 2008

(87) PCT Pub. No.: WO2007/009217
PCT Pub. Date: Jan. 25, 2007

(65) Prior Publication Data
US 2008/0299646 A1     Dec. 4, 2008

Related U.S. Application Data

(60) Provisional application No. 60/701,497, filed on Jul. 22, 2005.

(51) Int. Cl.
*C12P 19/06*     (2006.01)

(52) U.S. Cl. ............ 435/104; 435/101; 435/23; 435/24; 536/114

(58) Field of Classification Search .................. 435/104, 435/101, 23, 24; 536/114
See application file for complete search history.

(56) References Cited

U.S. PATENT DOCUMENTS 3,966,618 A    6/1976 Colegrove
5,702,927 A  * 12/1997 Murofushi et al. ........... 435/104

FOREIGN PATENT DOCUMENTS

WO         01193302 A2       8/1989
WO     WO 2006/053761       5/2006

OTHER PUBLICATIONS

International Search Report and Written Opinion of the International Searching Authority for PCT Application No. PCT/CA2006/001136, mailed Nov. 2, 2006.

\* cited by examiner

*Primary Examiner* — Tekchand Saidha
(74) *Attorney, Agent, or Firm* — Myers Bigel Sibley & Sajovec, P.A.

(57) ABSTRACT

The invention provides a process for producing polysaccharide gum comprising extracting a plant material with an aqueous solvent to produce a polysaccharide gum-containing extract; contacting the extract with at least one proteolytic enzyme to at least partially digest proteins in the extract; adding an organic solvent to the extract to precipitate the polysaccharide gum; and collecting the precipitated polysaccharide gum.

14 Claims, No Drawings

PROCESS FOR PRODUCING POLYSACCHARIDE GUM

CROSS-REFERENCE TO RELATED APPLICATIONS

This application is a 35 U.S.C. §371 national phase application of International Application Serial No. PCT/CA2006/001136 filed Jul. 12, 2006 which claims the benefit, under 35 U.S.C. §119(e), of U.S. Provisional Application No. 60/701,497, filed Jul. 22, 2005, the entire contents of each of which are incorporated by reference herein in their entireties. The above PCT International application was published in the English language as International Publication No. WO 2007/009217.

FIELD OF THE INVENTION

This invention relates to polysaccharide gum and to methods for producing polysaccharide gum from plant materials.

BACKGROUND OF THE INVENTION

In recent years, there has been an increasing interest both in the medical profession and in the general public in improved nutrition and healthy eating. As a result of this interest, there is a growing market for natural, plant-based food additives and food supplements.

Among these are plant-derived polysaccharide gums which can be used as dietary soluble fibre in functional foods and natural health products, as thickeners and stabilisers in the food industry, as moisturisers in cosmetics, as lubricants for personal use and as a basis for artificial saliva and tears for medical use.

Soluble dietary fibre components such as flax polysaccharide gum have been shown to reduce serum triglyceride and cholesterol levels and assist in management of serum glucose levels in animals. In humans, also, dietary fibre has been shown to be a vital component of a healthy diet, imparting a wide range of benefits for cardiovascular health, gastrointestinal health, immune function, weight control and cancer prevention.

Polysaccharide gums or mucilages can be obtained from a variety of plants including cereals, pseudocereals, legumes and oilseeds.

Polysaccharide gums have traditionally been extracted from plant materials with water or an aqueous solution, followed by alcohol precipitation of the gums. This process, however, also results in protein extraction and precipitation and the gum preparation produced contains a large amount of protein, which affects the physical, chemical and biological properties of the gum.

One excellent source of polysaccharide gum is flaxseed and extraction of gum from flax meal, the residue after oil extraction, is especially attractive as providing a commercial use for the meal which otherwise has had little application for human food use. Contamination of the gum with protein is, however, exacerbated when meal is used as starting material. For example, when such a process is employed on flaxseed meal, the resulting product can contain up to 60% protein (U.S. Pat. No. 5,925,401).

One approach to reducing protein contamination of gum is described in U.S. Pat. No. 2,593,528 which teaches fractionation of flaxseed into hull and kernel fractions and extraction of gum from the hull fraction alone.

Canadian Patent Application No. 2,462,538 describes the production of a "fibre-rich fraction" from oilseed meal but their initial treatment of the meal with a mixture of polysaccharidases would not yield high molecular weight polysaccharide gum. The "fibre fraction" also contained high levels of lignin.

U.S. Pat. No. 6,482,430 describes the production of a gelling hemicellulose from bran, which has a low protein content.

There remains a need for improved processes, suitable for commercial scale use, to produce high quality polysaccharide gum with minimal protein contamination.

SUMMARY OF THE INVENTION

The invention provides a process for producing polysaccharide gum comprising extracting a polysaccharide containing plant material with an aqueous solvent to produce a polysaccharide gum-containing extract; contacting the extract with at least one proteolytic enzyme to at least partially digest proteins in the extract; adding an organic solvent to the extract to precipitate the polysaccharide gum; and collecting the precipitated polysaccharide gum.

The plant material may be, for example, a seed meal, flour, or cake, for example flax meal.

The extract produced by extraction with the aqueous solvent may be adjusted to an acidic pH, for example about pH3 to about pH5, for example about pH4, to partially precipitate the protein of the extract and the precipitated protein is removed before the extract is contacted with the proteolytic enzyme.

The aqueous solvent may be water and the extraction is carried out at a temperature in the range of 75° C. to 80° C. for a suitable period of time.

The proteolytic enzyme may be an endopeptidase enzyme and the pH of the extract is adjusted to a pH in range of about pH6 to about pH8 when the extract is contacted with the proteolytic enzyme.

The proteolytic enzyme may be bromelain and the pH of the extract is adjusted to about pH6.2.

The extract may be purified, for example by ultrafiltration or by clay/charcoal extraction, before addition of the organic solvent.

The seed meal or flour used in the process may be substantially oil-free seed meal or minimally processed seed meal.

DETAILED DESCRIPTION OF THE INVENTION

The present invention provides a process for preparing polysaccharide gum from a plant material by extracting the plant material with an aqueous solvent, treating the extract with a proteolytic enzyme to at least partially digest extracted proteins and fractionating the resulting mixture to provide polysaccharide gum of high purity and a protein hydrolysate useful as a food additive or as a source of angiotensin converting enzyme (ACE) inhibitors.

Suitable plant materials include whole or crushed seeds, seed fractions, seed meal (i.e. the non-oil portion of oilseeds after total or partial oil extraction), and flours (i.e. the ground seed of a non-oil producing plant such as a cereal or a legume).

Polysaccharide gum-containing plants to which the process of the invention can be applied include cereals, pseudocereals, legumes, oilseeds, herbs, spices, and also yeasts and fungi and cell cultures from gum-containing plants. Examples of plants to which the process may be applied include flax, false flax (*Carmelina sativa*), fenugreek (*Trigonella foenum graecum* L.), mustards, psylluim, guar, locust bean, tara, tamarind, aloe, chia, okra, oat, barley, wheat, sorghum, millet, ginseng and mushrooms.

Plants such as flaxseed, which are good sources of polysaccharide gum, are also rich in phytochemicals such as lignan (SDG), phenolic acids, flavonoids and phytic acid. Such phytochemicals are known to inhibit some enzymes and are potential inhibitors of proteolytic enzymes and proteinase inhibitors have been reported in flaxseed (Lorenc-Kubis et al., (2001), Chembiochem., v. 8, pp. 45-51). The inventors have found, however, that crude, unpurified extracts resulting from co-extraction of polysaccharide gum and protein, even from plant materials of high protein content, can be successfully treated with proteolytic enzymes, thus providing a convenient process for producing polysaccharide gum without undesirable levels of contaminating protein.

The process of the invention has been shown to produce high quality polysaccharide gum from substantially completely defatted flaxseed meal (by prepressing (expeller), solvent extraction and toaster, leaving less than 5% w/w residual oil content) and from minimum processed flaxseed meal (no solvent extraction, residual oil typically 10-15%).

Suitable aqueous solvents for initial extraction of the plant material include water, acidic water, alkaline water, saline, buffers such as phosphate buffer, glycerol and ammonia. The plant material may be mixed with the aqueous solvent at a temperature in the range of 20° C. to 90° C., for example 75° C. to 80° C., for a period in the range of 30 minutes to 6 hours, for example 1 hour to 2 hours, with optional stirring or other agitation.

A wide range of pH values may be used for the extraction, for example from pH5 to 10, a range of pH 6 to 8 being preferred.

Plant material may be mixed with the solvent at a ratio in the range of 5 to 50:1 (solvent:plant material, by weight), for example at a ratio of 10 to 15:1 (solvent:plant material).

The aqueous extract is then separated from residual plant material by any suitable method such as filtration or centrifugation, the extract is adjusted to a pH suitable for a selected proteolytic enzyme and the selected proteolytic enzyme is added to the extract.

Proteolytic enzymes from a variety of sources may be used, including exopeptidases and endopeptidases, the latter being preferred. Suitable enzymes include bromelain, chymopapain, chymotrypsin, papain, pepsin, pronase, trypsin and microbial protease. More than one proteolytic enzyme may be employed. All of these enzymes are available commercially. Where a high viscosity gum is required, the selected proteolytic enzyme should be free of carbohydrate-degrading enzymes.

Where lower gum viscosities are acceptable, for example for promotion of immune function and gastrointestinal health, the presence or absence of carbohydrate-degrading enzymes is less critical.

The amount of proteolytic enzyme used will depend on the purity and activity of the enzyme, the length of time allowed for proteolysis and the protein level of the extract, as will be understood by those of skill in the art, who can readily determine suitable proteolysis conditions.

Those of skill in the art can determine from the relevant literature the appropriate pH range and incubation temperature for optimal activity of a particular enzyme. Typical incubation temperatures are in the range of 45° C. to 75° C. The length of incubation time is affected by the amount of protein in the extract and by the concentration of enzyme employed. Typically, proteolysis is carried out for a time in the range from about 30 minutes to 2 to 3 hours. Proteolytic action is terminated by heating the mixture.

An organic solvent such as an alcohol is then added to the extract to precipitate polysaccharide gum and the precipitated gum is collected by a suitable method such as filtration or centrifugation. Suitable organic solvents include lower alkyl alcohols such as ethanol, methanol, and 2-propanol, and acetone, ethyl acetate, butanol, 1,3 dioxolane or mixtures of these. The organic solvent should be added to the extract to give a final level of at least 40% v/v of the organic solvent in the mixture. Precipitation of gum may also be carried out using ammonium sulphate, DMSO, quaternary ammonium salts and cationic detergents such as cetyltri-methylammonium (CTA) or cetylpyridium (CP), although an alcohol is the preferred precipitating agent for preparation of food products.

The extract after proteolysis is preferably subjected to some purification prior to alcohol precipitation. For example, the extract is treated with clay/charcoal and filtered, as described herein, or is subjected to ultrafiltration, for example with a membrane of 50,000 molecular weight cut off.

Residual moisture in the gum can be removed by pressing followed by final drying by freeze drying, vacuum drying or oven drying. Removed alcohol can be reclaimed by evaporator or distillation. Such methods are described, for example, in "Industrial Gums: Polysaccharides and their Derivatives" $3^{rd}$ edition, Ed. Whistler et al., (1993), Academic Press, Toronto.

The polysaccharide gum produced by the process of the invention has high viscosity, indicating the integrity of the polysaccharide polymers, and a very low protein content.

For use in products, the precipitated gum can be redissolved/rehydrated in water in order to have viscosity fully developed. Other ingredients such as fragrance, emulsifiers, preservatives, and oil can also be incorporated, if the gum is used for cosmetics. The polysaccharide gum (dry powder or rehydrated) can also be used as a functional ingredient/supplement in various dietary products such as beverages and food products such as bars.

In a further embodiment of the invention, the initial aqueous extract is adjusted to an acid pH to precipitate proteins having an acidic iso-electric point and this precipitate is removed before the proteolytic enzyme is added. The precipitated proteins can be used as a nutritional supplement for human or animal foods. The supernatant is then adjusted to the desired pH for proteolytic enzyme action and proteolysis is carried out, followed by alcohol precipitation of gum, as described above.

EXAMPLES

The examples are described for the purposes of illustration and are not intended to limit the scope of the invention.

Methods of chemistry and protein and polysaccharide biochemistry referred to but not explicitly described in this disclosure and examples are reported in the scientific literature and are well known to those skilled in the art.

Methods: Flow Characteristics Measured by a Controlled Stress Rheometer.

A controlled stress rheometer (AR 1000N Rheometer from TA Instruments Inc., New Castle, Del.) was used to evaluate the flow characteristics of gum solutions. This rheometer was equipped with cone & plate and parallel plate geometries, autogap set, as well as a temperature control system (Peltier plate). A cone (6.0 cm diameter standard steel cone, 1:59 degree angle) and plate geometry was used throughout. The gap between the cone & plate (truncation) was set at 68 µm. The sample was placed between two circular plates, the lower of which was flat and horizontally mounted. The upper plate had the form of an inverted cone, truncated at the tip, with the virtual cone tip located in the plane of the surface of the lower plate. The lower plate was driven at a given rotational speed or angular frequency, and a simple numerical conversion provided the shear rate. Stress was transmitted by the sample to the upper plate, causing it to rotate against a precalibrated torsion bar on which the plate is suspended. The rotation was monitored by a linear displacement transducer, and the shear stress was calculated. Concentricity of the upper and lower plates was maintained by an annular air bearing of negligible friction.

Example 1

Fully defatted flax meal was obtained from Landmark Feeds Inc (Winnipeg, Manitoba). The meal contained 2.36% fat, 33.81% protein, 6.70% ash, and 0.73% lignan (SDG) on a dry weight basis (dwb). 100 g meal was extracted with 1500 ml water at 75° C. for 2 hours with stirring. The mixture was then centrifuged, the supernatant was decanted and the gel-like layer on top of the meal was scraped and rinsed off and combined with the supernatant, to give Extract I. 30-35 g Extract I and 60 g spent meal, on a dry weight basis, were produced. Extract I contained 1.3% dwb SDG, 33-34% protein and a significant amount of soluble gum.

The pH of Extract I was adjusted to 6.2, 1.2 g bromelain (Enzyme Development Company, New York, N.Y.) was added and the mixture was incubated at 55° C. for 4 hours. Enzyme activity was terminated by heating the incubation mixture at 90° C. for 30 minutes.

The mixture was clarified by adding bleaching clay (25 g) and activated carbon (2 g) and incubating at 90° C. for one hour. The slurry was filtered through a filter paper with a Celite filter aid (100 g for bed) in a large Buchner funnel. Gum was precipitated by adding an equal volume of 95% ethanol to the clarified extract slowly with gentle agitation. The precipitated gum was recovered by filtration and was designated "gum concentrate". The alcoholic solution remaining after filtration was used to recover the alcohol using a rotary evaporation system. The aqueous phase left in the evaporation system after most of alcohol had been stripped off was designated "protein hydrolysate".

All fractions were freeze dried and samples were tested for protein and ash content.

7-8 g protein hydrolysate and 7-8 g gum concentrate were obtained from 100 g of fully defatted flax meal. The gum concentrate contained 4-5% protein (dwb) and was free of SDG. The protein hydrolysate contained 30-38% (dwb) protein, and 0.2-0.8% (dwb) of SDG.

Example 2

A further 100 g portion of the fully defatted flax meal of Example 1 was extracted with 1500 ml water at 75° C. for 2 hours with stirring. The mixture was then centrifuged, the supernatant was decanted and the gel-like layer on top of the meal was scraped and rinsed off and combined with the supernatant to give Extract I. 30-35 g Extract I and 60 g spent meal, on dry weight basis, were produced.

The pH of Extract I was adjusted to 4 to precipitate protein. The protein precipitate (protein concentrate) was collected by centrifuging and the pH of the supernatant (Extract II) was adjusted to about 6.2 before incubation with bromelain (1.25 g, for 4 hours at 55° C.). To terminate enzyme activity, the incubation mixture was heated to 90° C. for 30 minutes.

The mixture was then clarified as described in Example 1. Gum was precipitated as described in Example 1.

All fractions were freeze dried and samples were tested for protein and ash content.

7-10 g protein concentrate, 4-5 g of gum concentrate, 8-10 g of protein hydrolysate and 60-66 g of spent meal was obtained from 100 g of fully defatted flax meal. The protein concentrate contained 57-60% protein, 5-6% ash, and 3-4% SDG. The gum concentrate contained 4-7% protein, 6-8% ash, and was free of detectable SDG. The protein hydrolysate contained 24-28% protein, 18-19% ash, and 1-2% SDG. The spent meal contained 36-39% protein and 7-8% ash (all percentages are on dry weight basis). The gum concentrate was fully rehydrated and dissolved in water. The viscosity of a 2.5% w/w gum solution was 0.25-0.30 Pa·s at 100 1/s shear rate. The rheological nature of flax gum is pseudoplastic (shear-thinning). The ash content of the protein hydrolysate can be reduced by desalting the hydrolysate before freeze drying.

Example 3

A further batch of fully defatted flax meal was obtained from Landmark Feeds Inc (Winnipeg, Manitoba). The meal contained 3.81% fat, 32.42% protein, and 6.08% ash on dry weight basis. The meal was processed as in Example 2.

14-16 g of protein concentrate, 4-5 g of gum concentrate, 8-10 g of protein hydrolysate, and 58-62 g of spent meal was obtained from 100 g of fully defatted flax meal. The protein concentrate contained 57-60% protein, 3-4% ash, and 3-4% SDG. The gum concentrate contained 6-7% protein and 5-9% ash. The protein hydrolysate contained 30-32% protein, 15-16% ash, and 1-2% SDG. The spent meal contained 33-34% protein and 6-7% ash. The viscosity of a 2.5% gum solution was 0.20-0.24 Pa·s at 100 1/s shear rate.

Example 4

The meal used in Example 1 was extracted at a meal/water ratio of 100 g meal:1000 ml water. The meal was otherwise processed as in Example 2.

10-12 g of protein concentrate, 5-6 g of gum concentrate, 8-10 g of protein hydrolysate, and 60-66 g of spent meal was obtained from 100 g of fully defatted flax meal. The protein concentrate contained 50-52% protein, and 1.2% SDG. The gum concentrate contained 4-7% protein, and was free of detectable lignan (SDG). The protein hydrolysate contained 23-24% protein. The spent meal contained 35-37% protein, and 0.57-0.65% lignan (SDG). The viscosity of a 2.5% gum solution was 0.20-0.25 Pa·s at 100 1/s shear rate.

Example 5

A further batch of the meal used in Example 1 was processed as in Example 2, but without charcoal filtration.

12-13 g of protein concentrate, 5-6 g of gum concentrate, 10-11 g of protein hydrolysate, and 60-66 g of spent meal was obtained from 100 g of fully defatted flax meal. The protein concentrate contained 50-52% protein, and 1.1% SDG. The gum concentrate contained 4-5% protein, and 0.03% lignan (SDG). The protein hydrolysate contained 24-29% protein, and 1.2% lignan (SDG). The spent meal contained 35-37% protein, and 0.57-0.65% lignan (SDG). The viscosity of a 2.5% gum solution was 0.4-0.42 Pa·s at 100 1/s shear rate.

Example 6

Minimum processed flax meal was obtained from Bioriginal Food and Science Corporation (Saskatoon, SK, Canada).

The meal contained 11.34% of fat, 37.62% of protein, and 4.10% of ash on a dry weight basis. The meal was treated as described in Example 2. 18-21 g of protein concentrate, 5-7 g of gum concentrate, 10-12 g of protein hydrolysate, and 55-60 g of spent meal was obtained from 100 g of minimum processed flax meal. The protein concentrate contained 61-66% protein, 3-4% ash, and 3-4% SDG. The gum concentrate contained 4-7% protein and 5-9% ash. The protein hydrolysate contained 32-33% protein, 16-20% ash, and 1-2% SDG. The spent meal contained 38-40% protein, 5-6% ash and 80-90% total dietary fibre. The viscosity of a 2.5% gum solution was 0.60-0.62 Pa·s at 100 1/s shear rate.

Example 7

A sample of the precipitated flax gum of Example 3 was rehydrated into a 2.5% gum solution. The solution was put into autoclavable bottles and autoclaved at 120° C. for 20 minutes. Viscosity at 100 1/s shear rate was reduced only very slightly from 0.23 Pa·s to 0.21 Pa·s after autoclaving.

The invention claimed is:

1. A process for producing polysaccharide gum comprising extracting a plant material with an aqueous solvent to produce a polysaccharide gum-containing extract; contacting the extract with at least one proteolytic enzyme to at least partially digest proteins in the extract; adding an organic solvent to the extract to precipitate the polysaccharide gum; and collecting the precipitated polysaccharide gum.

2. The process of claim 1 wherein the plant material is selected from the group consisting of whole seeds, crushed seeds, a seed fraction, a seed meal and a flour.

3. The process of claim 1 wherein the extract produced by extraction with the aqueous solvent is adjusted to an acidic pH to partially precipitate the protein of the extract and the precipitated protein is removed before the extract is contacted with the proteolytic enzyme.

4. The process of claim 1 wherein the aqueous solvent is water and the extraction is carried out at a temperature in the range of 20° C. to 90° C. for a suitable period of time.

5. The process of claim 1 wherein the proteolytic enzyme is an endopeptidase enzyme and the pH of the extract is adjusted to a pH in range of about pH 4.0 to about pH 11.0 when the extract is contacted with the proteolytic enzyme.

6. The process of claim 1 wherein the proteolytic enzyme is selected from the group consisting of bromelain, chymopapain, chymotrypsin, papain, pepsin, pronase, trypsin and microbial protease.

7. The process of claim 6 wherein the proteolytic enzyme is bromelain, and the pH of the extract is adjusted to about pH 6.2.

8. The process of claim 1 wherein the extract is clarified before addition of the organic solvent.

9. The process of claim 1 wherein the organic solvent is 95% ethanol.

10. The process of claim 1 wherein the plant material is from a cereal, a legume, a pseudocereal, a herb, a spice, a yeast, a fungus or a cell culture.

11. The process of claim 1 wherein the plant material is flax meal.

12. A process for producing polysaccharide gum comprising extracting a plant material with an aqueous solvent to produce a polysaccharide gum-containing extract; adjusting the extract to an acidic pH of about pH 3.0 to about pH 6.0 to partially precipitate the protein of the extract; removing the precipitated protein from the extract; contacting the extract with at least one proteolytic enzyme to at least partially digest proteins in the extract; adding an organic solvent to the extract to precipitate the polysaccharide gum; and collecting the precipitated polysaccharide gum.

13. A process for producing polysaccharide gum comprising extracting substantially oil free seed meal or minimally processed seed meal with an aqueous solvent to produce a polysaccharide gum-containing extract; contacting the extract with at least one proteolytic enzyme to at least partially digest proteins in the extract; adding an organic solvent to the extract to precipitate the polysaccharide gum; and collecting the precipitated polysaccharide gum.

14. The process of claim 12 wherein the acidic pH is about pH 4.0.

* * * * *

UNITED STATES PATENT AND TRADEMARK OFFICE
CERTIFICATE OF CORRECTION

| | | |
|---|---|---|
| PATENT NO. | : 7,910,339 B2 | Page 1 of 1 |
| APPLICATION NO. | : 11/996072 | |
| DATED | : March 22, 2011 | |
| INVENTOR(S) | : Chang et al. | |

It is certified that error appears in the above-identified patent and that said Letters Patent is hereby corrected as shown below:

On the Title Page:
Item (56) References Cited, Foreign Patent Documents, Line 1:
  correct "WO 01193302 A2   8/1989"
  to read -- JP 01193302 A2   8/1989 --

Signed and Sealed this
Fourth Day of October, 2011

David J. Kappos
*Director of the United States Patent and Trademark Office*

UNITED STATES PATENT AND TRADEMARK OFFICE
CERTIFICATE OF CORRECTION

PATENT NO. : 7,910,339 B2
APPLICATION NO. : 11/996072
DATED : March 22, 2011
INVENTOR(S) : Chang et al.

It is certified that error appears in the above-identified patent and that said Letters Patent is hereby corrected as shown below:

In the Patent:

Column 5, Line 21: Please correct "Al2O$_3$ to read -- Al$_2$O$_3$ --
Line 25: Please correct "Al2O$_3$" to read -- Al$_2$O$_3$ --

Column 6, Line 14: Please correct "W03" to read -- WO$_3$ --

Column 18, Example 6a, Lines 55-62: Please delete duplicate compound

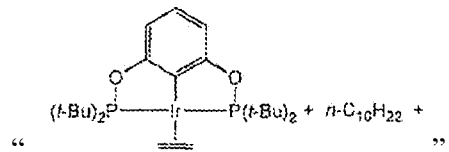

Column 19, Example 6a, Lines 19-26: Please delete duplicate compound

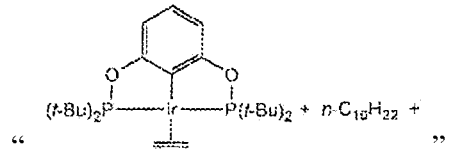

Column 20, Example 7, Line 50: Please correct "+ C.and" to read -- + C$_{19}$ and --

Column 26, Line 57: Please correct "free ≠" to read -- free γ --

Signed and Sealed this
Eleventh Day of October, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,910,339 B2 | Page 1 of 1 |
| APPLICATION NO. | : 11/996072 | |
| DATED | : March 22, 2011 | |
| INVENTOR(S) | : Peter R. Chang et al. | |

It is certified that error appears in the above-identified patent and that said Letters Patent is hereby corrected as shown below:

This certificate supersedes the Certificate of Correction issued October 11, 2011. The certificate is vacated since errors appearing on the Certificate of Correction does not correspond to text in the printed patent. The Certificate of Correction should not have been issued.

Signed and Sealed this
Thirty-first Day of January, 2012

David J. Kappos
*Director of the United States Patent and Trademark Office*